US012172957B2

(12) United States Patent
Navarro Fuertes et al.

(10) Patent No.: US 12,172,957 B2
(45) Date of Patent: Dec. 24, 2024

(54) **ATTRACTANT COMPOSITION FOR THE SPECIES *DELOTTOCOCCUS ABERIAE*, METHODS FOR THE MONITORING, DETECTION AND/OR CONTROL OF THE PEST**

(71) Applicants: Ecologia y Proteccion Agricola, S.L., Carlet (ES); Universitat Politécnica de València, Valencia (ES)

(72) Inventors: Ismael Navarro Fuertes, Carlet (ES); Sandra Vacas González, Valencia (ES); Vicente Navarro Llopis, Valencia (ES); Javier Marzo Bargués, Carlet (ES); Alejandro Carbonell Garcia, Carlet (ES); Jaime Primo Millo, Valencia (ES)

(73) Assignees: Ecología y Protección Agricola, S.L., Carlet (ES); Universitat Politècnica de Valencia, Valencia (ES)

( * ) Notice: Subject to any disclaimer, the term of this patent is extended or adjusted under 35 U.S.C. 154(b) by 791 days.

(21) Appl. No.: 17/293,495

(22) PCT Filed: Nov. 11, 2019

(86) PCT No.: PCT/ES2019/070770
§ 371 (c)(1),
(2) Date: May 13, 2021

(87) PCT Pub. No.: WO2020/099705
PCT Pub. Date: May 22, 2020

(65) Prior Publication Data
US 2022/0002222 A1  Jan. 6, 2022

(30) Foreign Application Priority Data

Nov. 13, 2018 (ES) .............................. ES201831098

(51) Int. Cl.
*C07C 69/145* (2006.01)
*A01M 1/02* (2006.01)
*A01N 37/02* (2006.01)

(52) U.S. Cl.
CPC ............. *C07C 69/145* (2013.01); *A01M 1/02* (2013.01); *A01N 37/02* (2013.01); *C07C 2601/10* (2017.05)

(58) Field of Classification Search
CPC ... C07C 69/145; C07C 2601/10; C07C 57/02; A01M 1/02; A01N 37/02
See application file for complete search history.

(56) References Cited

FOREIGN PATENT DOCUMENTS

| WO | WO-2014115172 A1 * | 7/2014 | ........... C07C 29/143 |
|----|-------------------|--------|------------------------|
| WO | WO 2020/090705    | 5/2020 |                        |

OTHER PUBLICATIONS

International Preliminary Report on Patentability Dated May 18, 2021 From the International Bureau of WIPO Re. Application No. PCT/ES2019/070770. (6 Pages).
Informe de Busqueda Internacional [International Search Report] and the Written Opinion Dated Apr. 8, 2020 From the International Searching Authority Re. Application No. PCT/ES2019/070770 and Its Translation of Search Report Into English. (10 Pages).
Mori "Pheromone Synthesis. Part 260: Synthesis of (±)-(anti-1,2-Dimethyl-3-Methylenecyclopentyl)Acetaldehyde, the Racemate of the Female-Produced Sex Pheromone of the Pinapple Mealybug (*Dysmicoccus brevipes*), and Its Syn-Isomer", Tetrahedron, XP029731874, 72(41): 6578-6588, Available Online Aug. 25, 2016.
Tena et al. "Native and Naturalized Mealybug Parasitoids Fail to Control the New Citrus Mealybug Pest *Delottococcus aberiae*", Journal of Pest Science, XP036164377, 90(2): 659-667, Published Online Nov. 29, 2016.

* cited by examiner

*Primary Examiner* — Robert A Wax
*Assistant Examiner* — John Seungjai Kwon

(57) ABSTRACT

The present invention relates to the compound (4,5,5-trimethyl-3-methylenecyclopent-1-en-1-yl)methyl acetate and to an attractant composition for insects of the species *Delottococcus aberiae* comprising said compound. The present invention also relates to an attractant device for *Delottococcus aberiae* comprising said compound or said composition, and to a method for the control and/or monitoring of the populations of insects of the species *Delottococcus aberiae*.

18 Claims, 2 Drawing Sheets

ATTRACTANT COMPOSITION FOR THE SPECIES *DELOTTOCOCCUS ABERIAE*, METHODS FOR THE MONITORING, DETECTION AND/OR CONTROL OF THE PEST

RELATED APPLICATIONS

This application is a National Phase of PCT Patent Application No. PCT/ES2019/070770 having International filing date of Nov. 11, 2019, which claims the benefit of priority of Spanish Patent Application No. P201831098 filed on Nov. 13, 2018. The contents of the above applications are all incorporated by reference as if fully set forth herein in their entirety.

FIELD AND BACKGROUND OF THE INVENTION

The present invention is comprised in the technical sector of agricultural pest control, particularly relating to an attractant product for insects of the species *Delottococcus aberiae*.

"Cotonet de les Valls", *Delottococcus aberiae* (De Lotto) (Hemiptera: Pseudococcidae), is a new citrus pest in the Mediterranean. The first individuals of *Delottococcus aberiae* were detected in 2009 in Benifairó de les Valls (Valencia), causing severe deformations in oranges and tangerines, which have caused their full commercial depreciation (Beltrà, A; García Marí, F; Soto, A. 2013. "Cotonet de les Valls", *Delottococcus aberiae*, nueva plaga de los cítricos. Levante Agrícola 419, 348-352). Furthermore, like with other Pseudococcidae, it feeds on sap and produces treacle, causing the proliferation of saprophytic fungi, as well as a decrease in the rate of photosynthesis and the loss of plant vigour.

This species is originally from Sub-Saharan Africa and its presence had only been described in some countries of Central and Southern Africa: Kenya, Mozambique, Swaziland, South Africa, Tanzania and Zimbabwe (Ben-Dov, Y., Miller, D. R., Gibson, G. A. P. 2013. ScaleNet, *Delottococcus aberiae*. 20 May 2013. http://www.sel.barc.usda.gov/catalogs/pseudoco/Delottococcusaberiae.htm), therefore its introduction in Spain had to be related to the importation of plant matter from one of these countries.

*Delottococcus aberiae* is a polyphagous insect mentioned in tropical, subtropical and temperate crops, such as coffee, guava or olives (De Lotto, G. 1961. New Pseudococcidae (Homoptera: Coccoidea) from Africa. Bull. Br. Mus. (Nat. Hist.) Entomol. 10: 211-238), but it had never been described before as damaging citrus. This is because of this recent invasion against which, unfortunately, there are no specific control means, as it is a new pest for citrus crops worldwide. In addition to the commercial depreciation of the fruit, the presence of this pest therein can cause serious quarantine issues for citrus exports as it is a new pest for citrus in Europe, restricted to Africa until now.

Today, the active ingredients recommended against pseudococcidae are mineral oil, spirotetramat, chlorpyrifos and chlorpyrifos-methyl (Urbaneja A., Catalán J., Tena A., Jacas, J. 2015. Gestión Integrada de Plagas de Citricos, http://gipcitricos.ivia.es.), with the last two being the most active against *Delottococcus aberiae*. Unfortunately, these ingredients are restricted in use, therefore alternative tools are required for handling this pest. With regard to biological control, it has been demonstrated that *Delottococcus aberiae* has a strong defensive response and is capable of encapsulating the eggs of several general pseudococcidae parasitoids, such as *Acerophagus angustifrons* (Gahan), *Anagyrus* sp. near *pseudococci* (Girault), and *Leptomastix algirica* Trjapitzin (Hymenoptera: Encyrtidae) (Tena, A., J. García-Bellón, and A. Urbaneja. 2017. Native and naturalized mealybug parasitoids fail to control the new citrus mealybug pest *Delottococcus aberiae*. J. Pest Sci. 90: 659-667). Considerable efforts are being made for the importation and release of parasitoids from the region of origin, but in the meantime, the only strategy that could be used in the short-term is to advance the action of *Cryptolaemus montrouzieri* by releasing this predatory coccinellid.

The detection and monitoring of populations of pseudococcidae is key to the improvement of its control both in agricultural and in ornamental ecosystems, but sometimes it consists of a laborious visual inspection of the plant material in the search for living forms and the count of all the stages of the insect. Alternatively, corrugated cardboard traps can be used for the seasonal sampling of live forms and/or glue traps for monitoring the flight of males (Martínez-Blay, V., Pérez-Rodríguez, J., Tena, A., & Soto, A. (2018). Density and phenology of the invasive mealybug *Delottococcus aberiae* on citrus: implications for integrated pest management. Journal of Pest Science, 91(2), 625-637). This last technique requires the availability of attractants specific to the species, such as sexual pheromones, which up until now were not available for *Delottococcus aberiae*.

Moreover, the use of these sexual pheromones is known in commercial treatments for the control of Coccoidea pests (*Aonidiella aurantii* Maskell (Scalebur®, Ecologia y Protección Agrícola, Valencia) and *Planococcus ficus* Signoret (CheckMate® VMB-XL, Suterra, Bend, USA)) by using techniques such as sexual confusion, in which the male is unable to find a female by means of the action of various mechanisms causing the interruption of copulation. However, none of the existing compounds has an effect on *Delottococcus aberiae*.

Therefore, there is a need to provide a compound which allows the control and monitoring specifically of the population of *Delottococcus aberiae*, and which, in addition to being effective, allows the use thereof in environmentally sustainable methods for control.

SUMMARY OF THE INVENTION

The present invention solves the problems described in the state of the art given that it provides an attractant compound for insects of the species *Delottococcus aberiae*.

Therefore, in a first aspect, the present invention relates to a compound of formula I (hereinafter compound of the present invention):

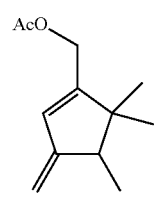

the stereoisomers and mixtures thereof.

In the present invention, the compound of formula I relates to (4,5,5-trimethyl-3-methylenecyclopent-1-en-1-yl) methyl acetate, the stereoisomers and mixtures thereof.

The compound of the present invention can exist as stereoisomers or mixtures of stereoisomers in any ratio, for example, the compound of the present invention can have an L-configuration, D-configuration, or it can be in racemic form.

In a second aspect, the present invention relates to an attractant composition for insects of the species *Delottococcus aberiae* (hereinafter composition of the present invention) comprising the compound of the present invention.

In a more particular aspect, the composition of the present invention comprises an amount of the compound of the present invention comprised between 0.001 to 1000 mg. Preferably, the effective amount is comprised in a range of between 0.001 to 200 mg.

As is known to a person skilled in the art, the amount of compound is variable based on the type of area, zone or object to be treated, the environmental conditions and the number of days of attraction required, as well as the particular ratio of enantiomers present in the (4,5,5-trimethyl-3-methylenecyclopent-1-en-1-yl)methyl acetate used.

In a more particular aspect, the composition of the present invention comprises at least one ingredient.

In the present invention, ingredient refers to any active substance incorporated in the composition to carry out at least one specific function.

More particularly, the ingredient is selected from antioxidants, radiation protection agents, insect control agents, pheromones, and mixtures thereof.

In the present invention, antioxidant refers to any substance capable of delaying or preventing oxidation of one or more components of the composition of the present invention. Preferably, the antioxidant agent of the composition of the present invention is selected from: ascorbic acid, erythorbic acid, sodium ascorbate, calcium ascorbate, butylated hydroxyanisole (BHA), butylated hydroxytoluene (BHT), sulfur dioxide, sodium erythorbate, ascorbyl stearate, propyl gallate, octyl gallate, dodecyl gallate, sodium hydrosulfite, lecithin, ascorbyl palmitate, tert-butylhydroquinone (TBHQ) and natural and/or synthetic tocopherols and any one combination of the aforementioned antioxidants.

In a more particular embodiment, in the attractant composition of the present invention, the antioxidant agent is comprised at a ratio of 1:1000 and 1:20 by weight with respect to the content by weight of (4,5,5-trimethyl-3-methylenecyclopent-1-en-1-yl)methyl acetate. The antioxidant agent is preferably at a ratio of 1:100 by weight with respect to the content by weight of (4,5,5-trimethyl-3-methylenecyclopent-1-en-1-yl)methyl acetate.

In the present invention, UV radiation protection agents refer to any compound capable of protecting and preserving against solar degradation one or more components of the composition of the present invention. The UV radiation protection agents of the present invention preferably refer to PABA derivatives, salicylates, cinnamates, benzophenones, benzimidazoles, anthranilates, terpene derivatives, inorganic oxides and any one combination of the preceding UV protection agents. They preferably refer to 4-aminobenzoic acid, 4-hydroxybenzophenone, 2-ethylhexyl salicylate, 2-ethylhexyl trans-4-methoxycinnamate, ethylhexyl 2-cyano-3,3-diphenylacrylate, titanium oxide and/or zinc oxide, and any one combination of the preceding UV protection agents.

In a more particular embodiment, in the attractant composition of the present invention, the UV radiation protection agent is comprised between a ratio 1:200 and 1:20 by weight with respect to the content by weight of (4,5,5-trimethyl-3-methylenecyclopent-1-en-1-yl)methyl acetate.

The UV radiation protection agent is preferably at a ratio of 1:50 by weight with respect to the content by weight of (4,5,5-trimethyl-3-methylenecyclopent-1-en-1-yl)methyl acetate.

In the present invention, insect control agent refers to a chemical substance which causes the death of the insect. More particularly, it refers to insecticides, more particularly to organochlorine insecticides, organophosphorus insecticides, carbamates, pyrethroids, neonicotinoids, tetramic acids, biorationals and a combination thereof.

In the present invention, pheromone is defined as any substance secreted by an animal and causing a reaction or a specific behaviour in a member of the same species, and particularly, a sexual pheromone is defined as that substance secreted by one of the sexes of the species and causing an attraction and copulation response in the other sex. Furthermore, kairomone refers to any substance secreted by an organism and being involved in the communication between individuals of different species, benefitting the organism that receives it.

In a more particular aspect, the composition of the present invention comprises at least one chemically acceptable excipient.

In the present invention, chemically acceptable excipient refers to any substance which is incorporated in the composition of the present invention to provide shape, consistency, flavour, smell, colour, etc. More particularly, the excipient is selected from binders, diluents, solvents, disintegrants, lubricants, dyes, sweeteners, flavour enhancers, preservatives and mixtures thereof.

In a more particular aspect, the composition of the present invention is presented in a formulation selected from emulsion, solution, dispersion, spray, liquid, gel, powder, granule, paste and pill.

In a more particular aspect, the composition of the present invention is incorporated in a carrier.

In the present invention, carrier refers to a substrate or matrix capable of carrying or containing the compound of the present invention or the composition of the present invention. More particularly, the carrier is selected from a polymer matrix, wood, ceramic, metal, leather, nylon, rubber, paraffin, wax, cotton, foam, textile material, granules, polymers, silicas, resins and adhesive tapes, inter alia.

In a more particular aspect, the compound of the present invention or the composition of the present invention is deposited, absorbed, adsorbed, sprayed or coated, in any physical or chemical form allowed, on the carrier, based on the nature of the compound, the composition and the carrier.

In a third aspect, the present invention relates to an attractant device for *Delottococcus aberiae* comprising a carrier containing the compound of the present invention or the composition of the present invention. In a particular embodiment, the device of the present invention comprises a trap.

In the present invention, trap refers to any device that traps and/or affects insects and/or holds them. In a particular embodiment, the trap comprises a substance that is toxic or pathogenic for the target insect. In a more particular embodiment, the trap is a surface comprising an adhesive.

In a particular embodiment, the carrier of the device of the present invention is contained in the trap.

In a particular embodiment, the carrier of the device of the present invention is separated from the trap.

In a fourth aspect, the present invention relates to a method for the control and/or monitoring of populations of *Delottococcus aberiae* (hereinafter, method of the present invention) comprising the use of the compound of the present invention or the composition of the present invention. More particularly, the method of the present invention comprises the use of the device of the present invention.

In a particular embodiment, the method for the control and/or monitoring is performed by attraction of male individuals belonging to the species of *Delottococcus aberiae*.

In another particular embodiment, the method for the control and/or monitoring is performed by sexual confusion of male individuals belonging to the species of *Delottococcus aberiae*.

In another particular embodiment, the method for the control and/or monitoring is performed by the death of male individuals belonging to the species of *Delottococcus aberiae*.

BRIEF DESCRIPTION OF THE SEVERAL VIEWS OF THE DRAWINGS

FIG. 1 depicts the detection of (4,5,5-trimethyl-3-methylenecyclopent-1-en-1-yl)methyl acetate in samples of volatiles from individuals of *Delottococcus aberiae* bred in a laboratory on lemons. The following are shown: (A) (4,5,5-trimethyl-3-methylenecyclopent-1-en-1-yl)methyl acetate synthetic as a racemate, (B) sample of volatiles from virgin females, (C) sample of volatiles from copulated females. It can be observed that the peak with a retention time of 24.24 min detected in the samples from virgin females (B) does not occur in the samples from copulated females (C), and it coincides with the synthetic sample of (4,5,5-trimethyl-3-methylenecyclopent-1-en-1-yl)methyl acetate (A).

FIG. 2 depicts the response of male *Delottococcus aberiae* to (4,5,5-trimethyl-3-methylenecyclopent-1-en-1-yl)methyl acetate in the test of choice under laboratory conditions: negative control vs. (4,5,5-trimethyl-3-methylenecyclopent-1-en-1-yl)methyl acetate. Percentages are with respect to the total individuals that showed activity. The negative control was the solvent pentane in all cases. There are significant differences (test $\chi^2$, P<0.05).

FIG. 3 depicts the mean (±standard error) of the number of male *Delottococcus aberiae* captured by the trap and the day of the test for the field attraction response to (4,5,5-trimethyl-3-methylenecyclopent-1-en-1-yl)methyl acetate. There are significant differences (ANOVA, LSD test at P<0.05).

DESCRIPTION OF SPECIFIC EMBODIMENTS OF THE INVENTION

Example 1: Detection of (4,5,5-trimethyl-3-tethylenecyclopent-1-en-1-yl)methyl acetate in Samples from Virgin Female *Delottococcus aberiae* by Means of Volatile Capture Techniques To capture the volatiles given off by female *Delottococcus aberiae* in different sexual states, laboratory-bred individuals kept on ecologically cultivated lemons at the Centro de Ecología Química Agrícola (Universitat Politècnica de València, Valencia) were used. Breeding is maintained in a controlled condition, at 23±2° C. and 60-70% relative humidity.

The volatiles given off by the insects were sampled by means of the aeration of the individuals and capture of the discharge in glass cartridges filled with the Porapak-Q adsorbent matrix. Groups of 200-300 individuals were placed on the breeding substrate in 5 l glass containers, passing through said containers a filtered air current of 0.4 l/min w. Every 7-8 days, the adsorbent material was washed with 20 ml of pentane to elute the captured substances. The eluents were analysed by means of gas chromatography coupled to mass spectrometry (GC-MS). The chromatographic analysis was performed in Clarus 600 GC-MS (PerkinElmer Inc.) equipment with ZB-5MS capillary column (30 m×0.25 mm i.d.×0.25 µm; Phenomenex Inc.) and the following temperature programme: 40° C. for 2 min; 5° C./min up to 180° C. and then increasing up to 280° C. at 10° C./min, maintaining at 280° C. for 1 min. Helium was used as the carrier gas with a flow rate of 1 ml/min. Detection was performed in electron impact mode (70 eV) and the temperature of the ionisation source and the transfer line was 200° C. and 250° C., respectively. Once an exclusive peak of the samples from virgin females was detected, it was isolated from the eluted mixture by means of the following method: (1) gravity chromatography of the total extract with pentane:diethyl ether mixtures (100:0, 95:5, 80:20, 0:100) as eluents; (2) location of the peak in the corresponding fraction by means of GC-MS; (3) isolation of the substance in the fraction by means of preparative GC. Preparative gas chromatography was carried out using Clarus 500 GC (Perkin Elmer) equipment with a flame ionisation detector and TRB-1 capillary column (30 m×0.53 mm i.d.×0.5 µm; Teknokroma Analitica SA, Sant Cugat del Vallès, Barcelona, Spain). The temperature of the oven was set to 40° C. for 2 min, later increasing at 3° C./min up to 100° C. and at 30° C./min up to 280° C., which is finally maintained for 12 min. Once isolated, structural elucidation was carried out with the data provided by the GC-MS spectrum and nuclear magnetic resonance (NMR) spectrum in 600 MHz Bruker brand equipment. Lastly, the spectra of the natural substance were compared with those of a sample synthesised by Ecología y Protección Agrícola SL (Carlet, Valencia).

Figure 1:
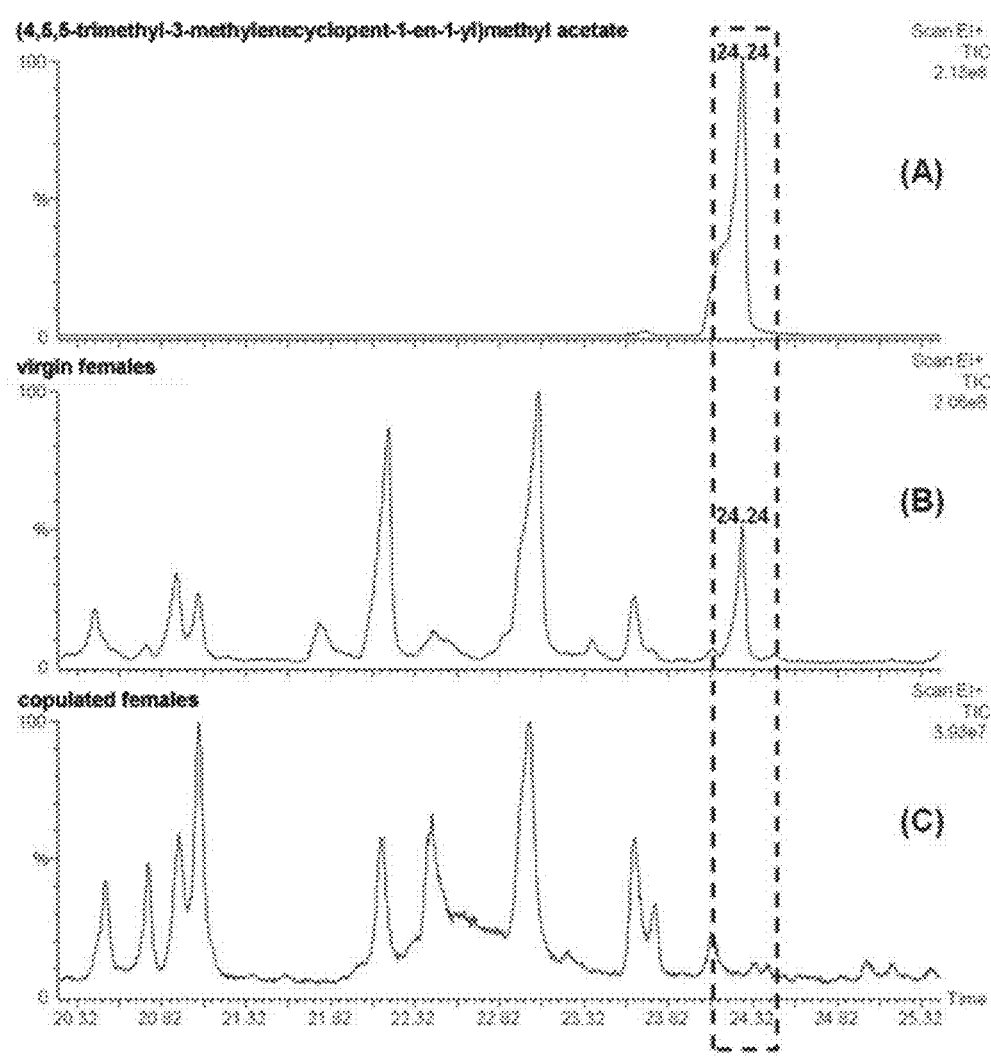
FIG. 1.

The chromatographic analysis revealed a peak which appeared exclusively in the samples of volatiles given off by virgin females and not in those from the females that had copulated or from immature individuals, as can be observed in FIG. 1. This peak corresponded with (4,5,5-trimethyl-3-methylenecyclopent-1-en-1-yl)methyl acetate, identified by means of spectrophotometric data, and subsequently confirmed by comparison with a synthetic sample produced in a laboratory as described in Example 2.

Example 2: Synthesis of (4,5,5-trimethyl-3-methylenecyclopent-1-en-1-yl)methyl acetate Synthesis thereof was carried out according to scheme 1 shown below:

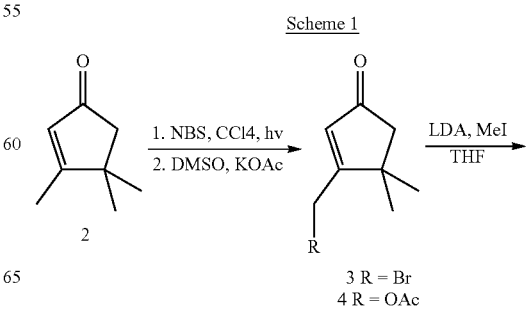

Scheme 1

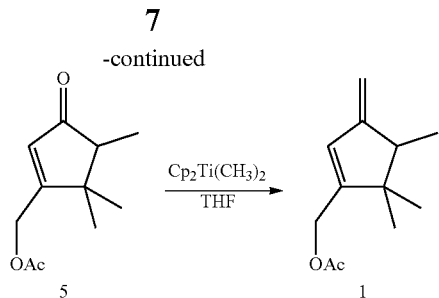

As can be observed in scheme 1, 500 mg of ketone 2 (Leviredend, M. L; Conia, Sur J. M. Sur la préparation de cyclopenténones par action de l'acide phosphorique sur les esters d'acides éthyléniques, Bulletin de la societè quimique de france, 8-9, 1970), were subjected to an allylic bromination reaction using 1.2 mg of N-bromosuccinimide in carbon tetrachloride catalysed by visible light irradiation with a 400 W power lamp for 6 hours at room temperature. After this time has lapsed, the solution was filtered and the solvent was evaporated under vacuum. The obtained residue is dissolved in 5 ml of DMSO and 1.5 equivalents of potassium acetate are added in portions under stirring. After 2 h have lapsed and the end of the reaction is confirmed by thin layer chromatography or gas chromatography, the mixture is poured over 40 ml of ethyl acetate and washed with water (15 ml×3) and brine (15 ml). The resulting solution is dried with anhydrous magnesium sulfate and the solvent is evaporated under vacuum. The residue is column-purified obtaining 400 mg (54% yield) of ketone 4. Spectroscopic data for ketone 4: $\delta_H$ (300 MHz, Chloroform-d) 5.99 (1H, t, J 1.8 Hz), 4.91 (2H, d, J 1.8 Hz), 2.36 (2H, s), 2.15 (3H, s), 1.28 (6H), s). $^{13}$C NMR (75 MHz, CDCl$_3$) δ 206.72, 181.22, 170.49, 127.55, 60.28, 52.19, 41.94, 27.35, 20.85. MS (70 eV) m/z: 43 (100), 67 (23), 79 (42), 95 (12), 110 (18), 125 (63), 140 (52), 167 (10), 182 (12, M+).

Ketone 4 (400 mg, 2.2 mmol) dissolved in THF (2 ml) is added drop-wise to a solution of LDA (1.25 eq) at −78° C. After 30 min has lapsed, 1 ml of methyl iodide is added and the solution is left to heat at room temperature for 2 h, and it is kept at this temperature for another 3 h. After this time has lapsed, the reaction mixture is poured over water and extracted with diethyl ether (2×50 ml). The organic phase is washed with brine (2×10 ml), dried with magnesium sulfate and the solvent is removed under vacuum. The crude reaction product is purified by column chromatography, obtaining 110 mg (25% yield) of methyl ketone 5. Spectroscopic data of ketone 5: δ H (300 MHz, Chloroform-d) 6.00 (1H, t, J 1.8 Hz), 4.92 (1H, d, J 1.8 Hz), 2.23 (1H, q, J 7.5 Hz), 2.14 (3H, s), 1.25 (3H, s), 1.09 (3H, s), 1.08 (3H, d, J 7.5 Hz). $^{13}$C NMR (75 MHz, CDCl$_3$) δ 209.01, 179.73, 170.51, 126.26, 60.59, 53.73, 44.90, 26.17, 23.91, 20.85, 9.73. MS (70 eV) m/z: 43 (100), 55 (23), 67 (33), 77 (14), 93 (38), 108 (20), 121 (14), 139 (57), 154 (32), 181 (22), 196 (8, M+).

300 milligrams (2.5 eq.) of biscyclopentadienyl titanium (II) dichloride in 10 ml toluene are suspended in a round-bottom flask and cooled at 0° C., and 0.85 ml (2 eq.) of a 3 M methyl magnesium chloride solution in THF are added to it. After 20 min has lapsed, it is left to heat at r.t. and is kept at this temperature for 1 h. 110 mg (0.56 mmol) of ketone 5 dissolved in 1 ml of toluene are added to the preceding mixture. The resulting solution is heated at 70° C. for 24 hours, at the end of which time it is cooled and poured over water. The mixture is extracted with diethyl ether (2×30 ml) and the pooled organic phases are washed successively with a 5% bicarbonate (2×15 ml) and brine (2×10 ml) solution. Lastly, the organic phase is dried with anhydrous magnesium sulfate and the solvent is removed under vacuum. The obtained product is purified by column chromatography, obtaining 16 mg of diene 1 (15% yield). Spectroscopic data for ketone 5: $\delta_H$ (300 MHz, Benzene-d$_6$) 6.06 (1H, s), 4.94 (1H, d, J2.5 Hz), 4.74 (1H, d, J 2.4 Hz), 4.70-4.55 (2H, m), 2.36 (1H, qt, J7.1, 2.5 Hz), 1.69 (3H, s), 0.93 (3H, d, J 7.1 Hz), 0.88 (3H, s), 0.75 (3H, s). $^{13}$C NMR (75 MHz, C$_6$D$_6$) δ 169.76, 156.66, 153.41, 129.24, 103.10, 60.76, 49.43, 47.55, 25.92, 22.09, 20.44, 12.42. MS (70 eV) m/z: 43 (72), 53 (12), 65 (14), 77 (21), 79 (19), 91 (40), 105 (20), 119 (100), 121 (72), 134 (22), 194 (10, M+).

The enantiomers making up the synthetic sample were separated by means of preparative chiral liquid chromatography in VWR LP-1100 equipment using a DAICEL 19335 AD-H chiral column (1×25 cm) with a 99:1 mixture of hexane:isopropanol as eluent. The sign of the specific optical rotation (levorotatory or dextrorotatory) of each of them was assigned in a Perkin-Elmer polarimeter using a sodium lamp (line D, 589 nm) and a cell 1 dm in length. Comparison by means of chiral gas chromatography allowed assigning the levorotatory isomer to the natural compound isolated from the females (Clarus 500 GC (Perkin Elmer) equipment with a flame ionisation detector and InertCap CHIRAMIX capillary column (30 m×0.25 mm i.d.×0.25 µm; GL Sciences Inc., Tokyo, Japan).

Example 3: Biological Tests on the Activity of (4,5,5-trimethyl-3-methylenecyclopent-1-en-1-yl)methyl acetate Under Laboratory Conditions The response of male *Delottococcus aberiae* to (4,5,5-trimethyl-3-methylenecyclopent-1-en-1-yl)methyl acetate was evaluated in the Centro de Ecologia Quimica Agricola (UPV, Valencia) by means of a test on the activity in a glass Petri dish. The tests were performed with light and under the same breeding conditions, at 23±2° C. and 60-70% relative humidity.

For these tests, males from breeding were also used, separated on Petri dishes right when the cottony cocoon begins to form. After pupating and finally emerging from the cocoon, the insects are observed under a binocular scope to confirm their state before being selected for the test.

The method used is described below: for each test, there were placed at opposite ends of the Petri dish a sample of (4,5,5-trimethyl-3-methylenecyclopent-1-en-1-yl)methyl acetate and a negative control (solvent pentane without activity), arranged on 1 cm$^2$ filter paper in an amount of 10 µl. Immediately, groups of males are carefully deposited on the test plate with the aid of a very fine brush. Therefore, the behaviour of the individuals with respect to the sources of stimulation is recorded for 10 min. Once the test has ended, the insects are discarded, such that each insect is exposed to olfactory stimuli only once. The obtained data were analysed by means of a Chi-squared test ($\chi$2 test, P<0.05).

Figure 2:
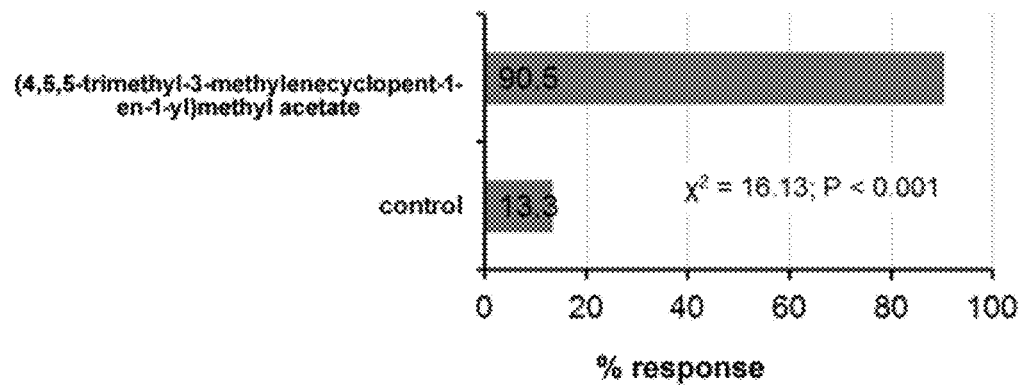
FIG. 2.

The results shown in FIG. 2 indicate that there is a significant attractant response in males to the pieces of filter paper impregnated with the synthetic pheromone.

Example 4: Field Tests on the Attraction Response in Male *Delottococcus aberiae*

The response in male *Delottococcus aberiae* to (4,5,5-trimethyl-3-methylenecyclopent-1-en-1-yl)methyl acetate was evaluated in two field tests performed in a citrus var. Marisol plot, located in Sagunto (Valencia), during the months of May-June 2018. In a first test, 3 blocks of 2 devices were installed, said devices being: (A) a device with carrier, without attractant substance and with a trap consisting of a white sheet with adhesive, (B) a device with carrier with bait containing 500 μg of (4,5,5-trimethyl-3-methylenecyclopent-1-en-1-yl)methyl acetate and a trap consisting of a white sheet with adhesive (95×150 mm) (in each block, the devices were located at a distance of 20 m from one another, whereas the distance between blocks was at least 30 m. The carriers loaded with (4,5,5-trimethyl-3-methylenecyclopent-1-en-1-yl)methyl acetate were septum-type carriers and were inserted in the centre of the trap.

The captures obtained in each of the traps were checked each week and the captured individuals were taken to the laboratory to be identified and counted. Traps in the same block were rotated each week.

The number of males captured per trap and day was compared by means of an analysis of variance (ANOVA; LSD test for comparison of the means, P<0.05), subject to transformation (ln(x+1)) of the data to homogenise the variance.

Figure 3:
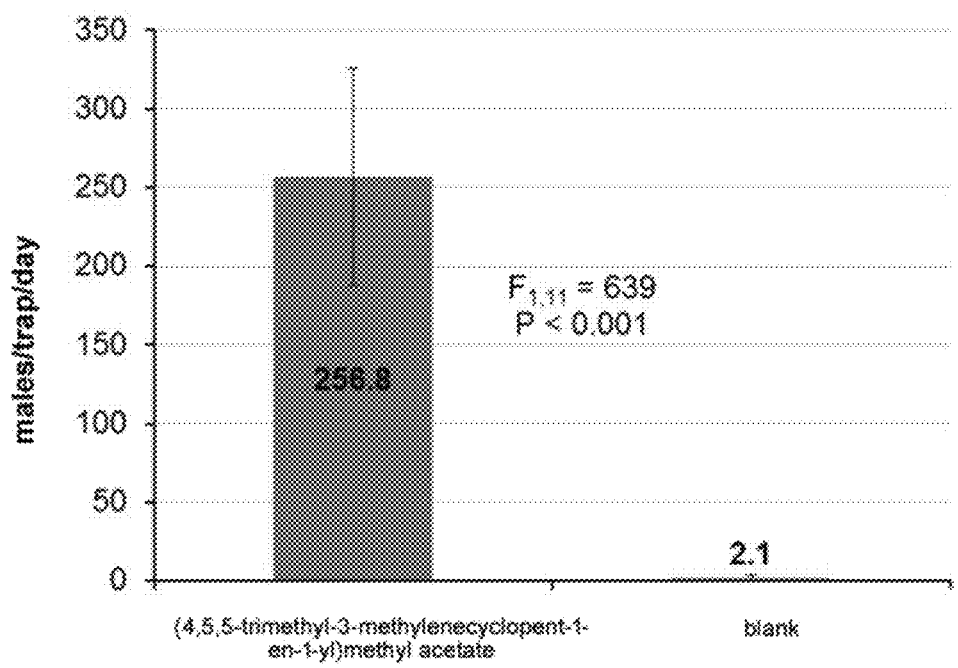
FIG. 3.

The results shows that the devices with bait containing (4,5,5-trimethyl-3-methylenecyclopent-1-en-1-yl)methyl acetate have a significantly higher attraction power than traps without attractant, as shown in FIG. 3. The tested load of (4,5,5-trimethyl-3-methylenecyclopent-1-en-1-yl)methyl acetate was 300 μg per septa.

The results of the analysis of the attractant content after 20 days show that the final content of the substance was 109 μg. Therefore, the mean emission for those 20 days is 9.45±2.13 μg/day. With respect to the level of obtained captures, the results can be observed in the following Table 1:

| Treatment | Male captures per trap and day |
|---|---|
| Pheromone | 61.0 |
| Pheromone | 52.7 |
| Pheromone | 58.0 |
| Control | 0.0 |
| Control | 0.3 |
| Control | 0.0 |

On average, 57.22 field captures per trap and day were obtained in the traps with bait with pheromone with respect to the 0.11 captures in the controls, which entails a significant difference in the analysis of variance (F=553.47; GI:1.5; P<0.001).

In a second test, this was performed in the same way as test 1, but device B included bait containing 100 μg of (4,5,5-trimethyl-3-methylenecyclopent-1-en-1-yl)methyl acetate.

The results of the analysis of the attractant content after 20 days show that the final content of the substance is 91 μg. Therefore, the mean emission for those 20 days is 0.55±0.42 μg/day.

On average, 9.14 field captures per trap and day were obtained in the traps with bait with pheromone with respect to the 0.06 captures in the controls, which entails a significant difference in the analysis of variance (F=5.22 GI:1.16; P<0.036)

With respect to the level of captures, the obtained results can be observed in Table 2:

| Treatment | Male captures per trap and day |
|---|---|
| Pheromone | 13.4 |
| Pheromone | 37.3 |
| Pheromone | 7.8 |
| Control | 0.1 |
| Control | 0 |
| Control | 0.1 |
| Pheromone | 4.7 |
| Pheromone | 15.3 |
| Pheromone | 1.3 |
| Control | 0.1 |
| Control | 0 |
| Control | 0 |
| Pheromone | 1.2 |
| Pheromone | 1.1 |
| Pheromone | 0.2 |
| Control | 0.1 |
| Control | 0.1 |
| Control | 0 |

Therefore, captures with emissions between 0.55±0.42 and 9.45±2.13 micrograms per day show significant capture.

The invention claimed is:

1. A compound of formula I,

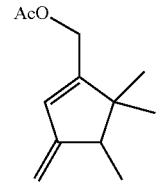

the stereoisomers and mixtures thereof.

2. An attractant composition for insects of the species *Delottococcus aberiae* comprising a compound according to claim 1.

3. The composition according to claim 2, comprising at least one other ingredient.

4. The composition according to claim 3, wherein said at least one other ingredient is selected from attractants, antioxidants, radiation protection agents, insect control agents, pheromones, kairomones, and mixtures thereof.

5. The composition according to claim 2, further comprising at least one chemically acceptable excipient.

6. The composition according to claim 5, wherein the excipient is selected from binders, diluents, disintegrants, lubricants, dyes, sweeteners, flavour enhancers, preservatives and mixtures thereof.

7. The composition according to claim 2, characterised in that the composition is presented in a formulation selected from emulsion, solution, dispersion, spray, liquid, gel, powder, granule, paste and pill.

8. The composition according to claim 2, characterised in that it is incorporated in a carrier.

9. The composition according to claim 8, wherein the carrier is a matrix.

10. An attractant device for *Delottococcus aberiae* comprising a carrier containing the compound according to claim 1.

11. The attractant device for *Delottococcus aberiae* according to claim 10, comprising a trap.

12. A method for controlling and/or monitoring *Delottococcus aberiae* populations, comprising subjecting *Delottococcus aberiae* populations to an effective amount of the compound according to claim 1.

13. A method for controlling and/or monitoring *Delottococcus aberiae* populations, comprising placing the device according to claim 10 at a location of the *Delottococcus aberiae* populations.

14. The method according to claim 12, wherein control is performed by attraction of male individuals belonging to the species of *Delottococcus aberiae*.

15. The method according to claim 12, wherein control is performed by sexual confusion of male individuals belonging to the species of *Delottococcus aberiae*.

16. The method according to claim 12, further comprising using an insect control agent to cause the death of male individuals belonging to the species of *Delottococcus aberiae*.

17. An attractant device for *Delottococcus aberiae* comprising a carrier containing a composition according to claim 2.

18. A method for controlling and/or monitoring *Delottococcus aberiae* populations, comprising subjecting the *Delottococcus aberiae* populations to the composition according to claim 2.

* * * * *